United States Patent
Perez et al.

(10) Patent No.: US 8,916,384 B2
(45) Date of Patent: Dec. 23, 2014

(54) PIPELINING ASSEMBLY FOR A BLOOD ANALYZING INSTRUMENT

(75) Inventors: Carlos A. Perez, Miami, FL (US); Jose M. Cano, Miami, FL (US); Joe C. Schorsch, Coconut Grove, FL (US); Viviana A. Vargas, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 194 days.

(21) Appl. No.: 13/443,581

(22) Filed: Apr. 10, 2012

(65) Prior Publication Data

US 2012/0208228 A1 Aug. 16, 2012

Related U.S. Application Data

(62) Division of application No. 12/492,270, filed on Jun. 26, 2009, now abandoned.

(51) Int. Cl.
| | |
|---|---|
| *G01N 35/00* | (2006.01) |
| *C12Q 1/02* | (2006.01) |
| *G01N 35/08* | (2006.01) |
| *G01N 35/10* | (2006.01) |

(52) U.S. Cl.
CPC .......... *G01N 35/0092* (2013.01); *G01N 35/085* (2013.01); *G01N 35/1097* (2013.01); *G01N 35/1004* (2013.01); *G01N 2035/00326* (2013.01); *G01N 2035/0093* (2013.01)
USPC ............................................ 436/43; 436/180

(58) Field of Classification Search
None
See application file for complete search history.

(56) References Cited

U.S. PATENT DOCUMENTS

| | | | |
|---|---|---|---|
| 3,690,833 | A | 9/1972 | Ferrari |
| 4,070,156 | A | 1/1978 | Moran et al. |
| 4,303,337 | A | 12/1981 | James et al. |
| 4,601,409 | A | 7/1986 | DiRegolo et al. |
| 4,683,212 | A | 7/1987 | Uffenheimer |
| 5,027,978 | A | 7/1991 | Roeser |
| 5,094,961 | A * | 3/1992 | del Valle et al. ............... 436/180 |

(Continued)

FOREIGN PATENT DOCUMENTS

| | | |
|---|---|---|
| JP | 06-258276 | 9/1994 |
| WO | 2006/084472 | 8/2006 |

OTHER PUBLICATIONS

International Preliminary Report on Patentability issued on Jan. 12, 2012 for International PCT Application Serial No. PCT/US2010/039440.

*Primary Examiner* — Jill Warden
*Assistant Examiner* — Benjamin Whatley
(74) *Attorney, Agent, or Firm* — K&L Gates LLP; Louis C. Cullman; Robert W. Winn

(57) ABSTRACT

A pipelining assembly for use in a blood analyzing instrument, methods for performing parallel pipelining functions, and methods for processing a plurality of prepared blood samples through a blood analyzing instrument. The pipelining assembly presented generally includes a first sample preparation chamber, a first queuing chamber in fluid communication with the first sample preparation chamber, and a first control valve between the first sample preparation chamber and the first queuing chamber. The pipelining assembly further includes a second sample preparation chamber, a second queuing chamber in fluid communication with the second sample preparation chamber, and a second control valve between the second sample preparation chamber and the second queuing chamber. An analysis chamber is provided to receive first and second prepared blood samples from the in first and second queuing chambers. The presented methods include steps for repeated processing of prepared blood samples through the blood analyzing instrument.

20 Claims, 3 Drawing Sheets

(56) References Cited

U.S. PATENT DOCUMENTS

| | | |
|---|---|---|
| 5,125,737 A | 6/1992 | Rodriguez et al. |
| 5,488,447 A | 1/1996 | Patton et al. |
| 5,616,501 A | 4/1997 | Rodriguez et al. |
| 5,630,935 A | 5/1997 | Treu |
| 5,631,730 A | 5/1997 | Chupp et al. |
| 5,652,937 A | 7/1997 | Earle et al. |
| 5,788,927 A | 8/1998 | Farrell et al. |
| 6,159,740 A | 12/2000 | Hudson et al. |
| 6,228,652 B1 | 5/2001 | Rodriguez et al. |
| 6,232,125 B1 | 5/2001 | Deka et al. |
| 6,488,894 B1 | 12/2002 | Miethe et al. |
| 6,558,625 B1 * | 5/2003 | Deves et al. ............. 422/78 |
| 6,675,987 B2 | 1/2004 | Soberunie et al. |
| 6,767,188 B2 | 7/2004 | Vrane et al. |
| 6,784,981 B1 | 8/2004 | Roche et al. |
| 6,979,569 B1 | 12/2005 | Carver et al. |
| 7,008,792 B2 | 3/2006 | Lopez et al. |
| 7,198,753 B1 * | 4/2007 | Campbell et al. ............ 422/68.1 |
| 7,208,319 B2 | 4/2007 | Lopez et al. |
| 7,410,615 B2 | 8/2008 | Krug et al. |
| 7,771,658 B2 * | 8/2010 | Larsen ....................... 422/82.01 |
| 2003/0013199 A1 | 1/2003 | Anderson et al. |
| 2003/0215957 A1 | 11/2003 | Lemmo et al. |
| 2005/0013738 A1 | 1/2005 | Schwalbe et al. |
| 2005/0056713 A1 | 3/2005 | Tisone et al. |
| 2005/0123970 A1 | 6/2005 | Ozbal et al. |
| 2007/0013906 A1 | 1/2007 | Kawate |
| 2007/0086923 A1 | 4/2007 | Li et al. |
| 2007/0089543 A1 | 4/2007 | Oku et al. |
| 2007/0212784 A1 * | 9/2007 | Okun ............................... 436/43 |
| 2007/0292308 A1 | 12/2007 | Horan et al. |
| 2008/0098828 A1 | 5/2008 | Li et al. |
| 2009/0062966 A1 * | 3/2009 | Pensak et al. .................. 700/285 |
| 2011/0137018 A1 * | 6/2011 | Chang-Yen et al. .......... 530/412 |

* cited by examiner

PIPELINING ASSEMBLY FOR A BLOOD ANALYZING INSTRUMENT

PRIORITY CLAIM

This application is a divisional that claims priority pursuant to 35 U.S.C. 120 to U.S. Non-Provisional patent application Ser. No. 12/492,270, filed on Jun. 26, 2009, which is hereby incorporated by reference in its entirety.

BACKGROUND OF THE INVENTION

1. Field of the Invention

The present invention relates to systems and methods for performing parallel pipelining functions in a blood analyzing instrument. More specifically, the present invention relates to a pipelining assembly for a blood analyzing instrument.

2. Background

In diagnosing different illnesses and disease states, it is common to analyze a patient's peripheral blood to differentiate and enumerate the various constituents within the blood, as well as to determine certain parameters or characteristics of those constituents. Various measurement techniques, alone or in combination, have been implemented in blood analyzing instruments to differentiate and enumerate the various constituents in a whole blood sample (WBS). Blood tests can include, for example, a Nucleated Red Blood Cell (NRBC) test, Differential test, or a Reticulocyte test. For example, U.S. Pat. No. 6,228,652 ("the '652 patent") discloses one such blood analyzing instrument. The blood analyzing instrument of the '652 patent includes a transducer for simultaneously measuring DC impedance, RF conductivity, light scattering, and fluorescence characteristics of a prepared blood sample passing through an analysis chamber, such as a flow cell. Additional systems are described in U.S. Pat. Nos. 5,125,737; 5,616,501; 6,232,125; 7,008,792; and 7,208,319.

Typical blood analyzing instruments distribute prepared samples using a mechanically driven multi-port distribution valve. Multi-port distribution valves have a common output port and two or more input ports. Multi-port distribution valves typically consist of two ceramic discs that are precisely machined to define port connections. One of the ceramic discs is held in place while the other disc is rotated using a stepper motor to align the output port to the user defined input ports. Input and output ports must be precisely aligned to ensure proper sample flow. Sensors must be used to keep track of disc rotation to ensure port alignment. Port misalignment can generate a series of system issues, including carryover, tubing pop-off due to pressure buildup, blood cell damage, and inconsistent and/or inefficient timing. Another disadvantage of multi-port distribution valves is that they typically require an analysis cycle to be processed through to completion before the system can be cleaned. In other words, the processes of analysis and cleaning must be performed in series.

Improving an instrument's throughput and efficiency is an important clinical objective. Presented herein is a pipelining assembly for performing parallel pipelining functions and avoiding the limitations of multi-port distribution valves.

BRIEF SUMMARY

Provided herein are various embodiments of a pipelining assembly for use in a blood analyzing instrument. Also provided herein are various embodiments of methods for performing parallel pipelining functions and methods for processing a plurality of prepared blood samples through a blood analyzing instrument. The pipelining assembly presented herein generally includes a first sample preparation chamber, a first queuing chamber in fluid communication with the first sample preparation chamber, and a first control valve between the first sample preparation chamber and the first queuing chamber. The first control valve is adapted to control the flow of fluid between the first sample preparation chamber and the first queuing chamber. Further, the pipelining assembly generally includes a second sample preparation chamber, a second queuing chamber in fluid communication with the second sample preparation chamber, and a second control valve between the second sample preparation chamber and the second queuing chamber. The second control valve is adapted to control the flow of fluid between the second sample preparation chamber and the second queuing chamber. An analysis chamber is provided in fluid communication with the first queuing chamber and the second queuing chamber to receive prepared blood samples. The presented methods include steps for using the presented pipelining assemblies for repeated processing of a plurality of prepared blood samples through the blood analyzing instrument.

BRIEF DESCRIPTION OF THE FIGURES

The accompanying figures, which are incorporated herein, form part of the specification and illustrate embodiments of a pipelining assembly for a blood analyzing instrument. Together with the description, the figures further serve to explain the principles of and to enable a person skilled in the relevant art(s) to make and use the pipelining assembly and methods described herein. In the drawings, like reference numbers indicate identical or functionally similar elements.

DETAILED DESCRIPTION OF THE INVENTION

The following detailed description of a pipelining assembly and methods for performing parallel pipelining functions refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware, software, and/or firmware. Any actual hardware, software, and/or firmware described is not meant to be limiting. The operation and behavior of the systems and methods presented are described with the understanding that modifications and variations of the embodiments are possible given the level of detail presented. For example, while the description provided incorporates the pipelining assembly into a blood analyzing instrument, the pipelining assembly and methods presented herein should not be limited to the environment of a blood analyzing instrument. One of skill in the art would readily understand how to incorporate the presented pipelining assembly and methods in alternative environments, such as, for example, flow cytometry systems, cell sorting systems, DNA analysis systems, etc.

Figure 1:
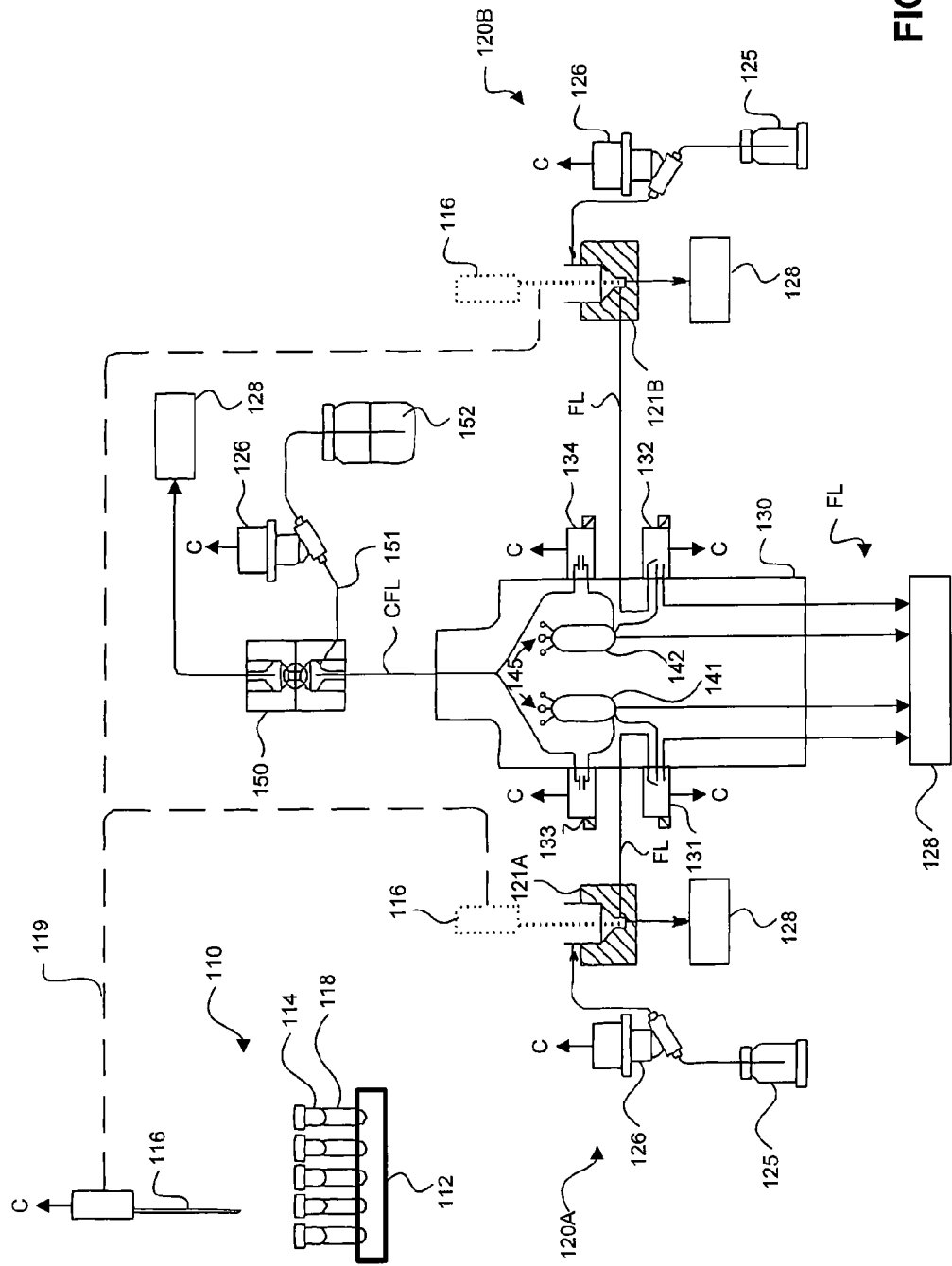
FIG. 1 is a schematic view of a pipelining assembly in accordance with one embodiment presented herein.

FIG. 1 is a schematic view of a pipelining assembly 100. In the embodiment presented, pipelining assembly 100 includes four main sub-systems: aspiration assembly 110, preparation assembly 120, manifold 130, and analysis chamber 150. While the pipelining assembly 100 is shown with only four main sub-systems, one of skill in the art would recognize that a complete blood analyzing instrument includes many other sub-systems such as a control assembly, a cleaning assembly, a data processing assembly, a display assembly, etc.

Aspiration assembly 110 includes a tray 112 holding one or more blood sample tubes 114. An aspiration needle 116 is used to aspirate whole blood sample 118 from one or more of sample tubes 114. (As would be understood by one of skill in the art, aspiration needle 116 can be used to aspirate the entirety of, or only a portion of, whole blood sample 118.) As such, aspiration needle 116 serves as means for receiving a blood sample. Additional means for receiving a blood sample would include structures equivalent to aspiration needle 116. In the embodiment shown, aspiration assembly 110 is coupled to and controlled by a system control processor C. In operation, and as shown in phantom, aspiration needle 116 draws whole blood sample 118 from one or more sample tubes 114 and delivers the whole blood sample 118 to one or more sample preparation assemblies 120. For example, in one embodiment, aspiration needle 116 is run along a track 119 to deliver a first whole blood sample 118 to a first sample preparation chamber 121A. Aspiration needle 116 is then returned along track 119 to tray 112 to aspirate a second whole blood sample 118 and thereafter deliver the second whole blood sample to a second sample preparation chamber 121B. Aspiration needle 116 can also be used to deliver portions of a single whole blood sample to multiple sample preparation chambers. In an alternative embodiment, multiple aspiration needles may be employed to deliver multiple whole blood samples to multiple sample preparation chambers. As such, aspiration assembly 110 serves as means for separating whole blood sample into a plurality of sample preparation chambers. Additional means for separating whole blood sample into a plurality of sample preparation chambers would include structures equivalent to aspiration assembly 110.

In the embodiment shown, each sample preparation assembly 120 includes a sample preparation chamber 121, at least one reagent source 125, and at least one pump 126. Pump 126 is controlled by system control processor C. In operation, system control processor C actuates pump 126 to deliver appropriate amounts of reagent and/or diluent to sample preparation chamber 121. Within sample preparation chamber 121, the blood sample is prepared for later analysis. Pump 126 can also be coupled to a source of cleansing fluid (not shown) to deliver cleansing fluid and thereby clean sample preparation chamber 121. As used herein, the verb "clean," and any conjugations thereof, is intended to mean rinsing or flushing with any non-sample fluid such as, for example, water, diluent and/or cleaning solution. The terms "diluent," "cleaning solution," and "cleansing fluid," are used interchangeably when used in the context of cleaning.

Figure 2:
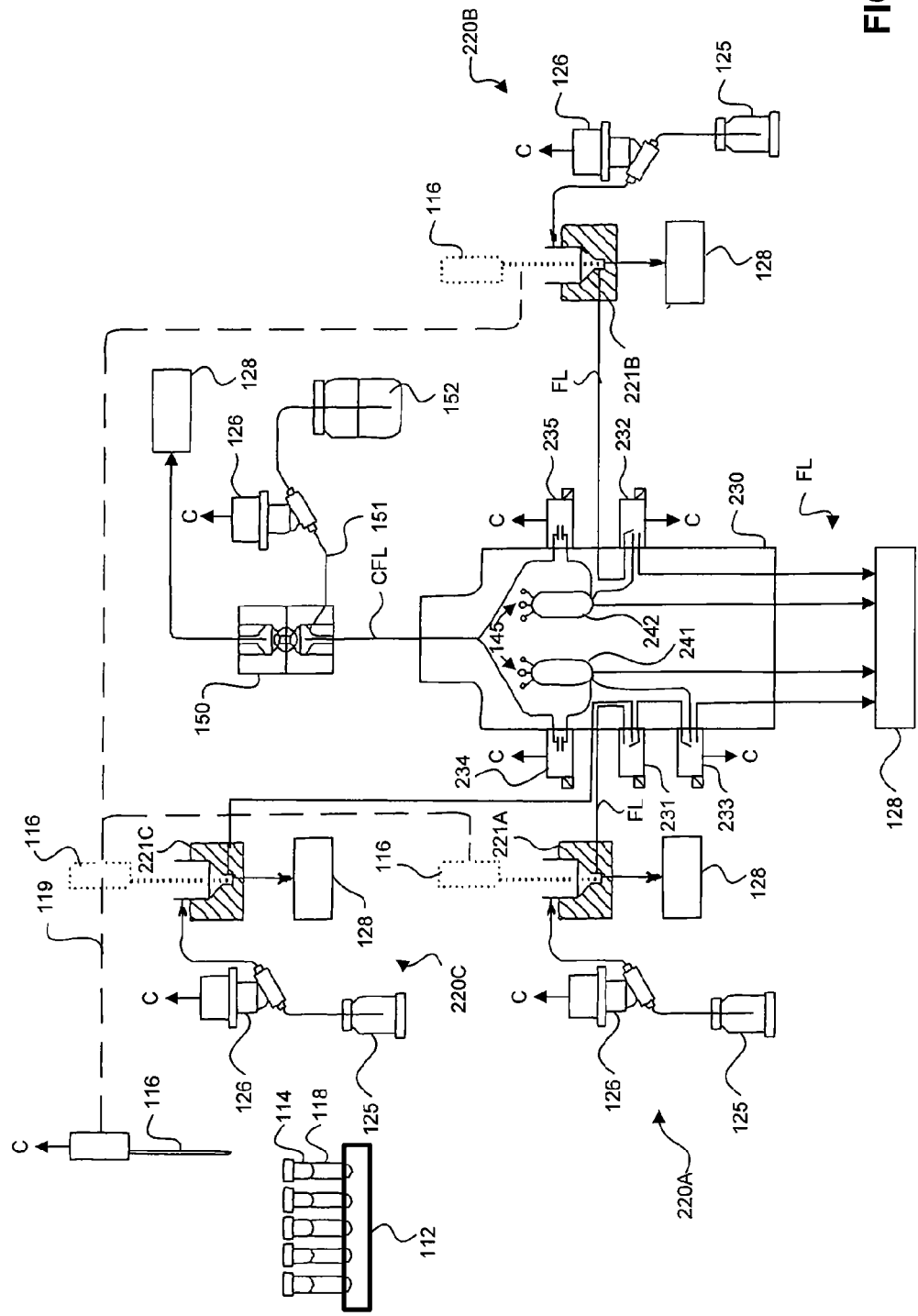
FIG. 2 is a schematic view of a pipelining assembly in accordance with an alternative embodiment presented herein.

It is understood that pipelining assemblies in accordance with the present invention are not limited to two sample preparation assemblies 120A, 120B. For example, FIG. 2 shows a pipelining assembly with three sample preparation assemblies 220A, 220B, and 220C. In other embodiments, any number of sample preparation assemblies can be employed. Sample preparation assembly 120 serves as means for preparing a prepared blood sample. Additional means for preparing a prepared blood sample would include structures equivalent to sample preparation assembly 120. As will be further explained below, the prepared blood sample is ultimately transferred to an analysis chamber 150 of the blood analyzing instrument.

Each sample preparation assembly 120 is also in fluid communication with a waste circuit 128. Waste circuit 128 can be used as both a source and a sump of excess fluid, including excess sample fluid, diluent, cleansing fluid, etc. Waste circuit 128, can be as simple as a passive container for dumping fluid, or can include vacuum and/or pressure controls for active manipulation of fluid. Waste circuit 128 can also be shutoff from the pipelining assembly via appropriately placed control valves. Further, waste circuit 128 can be internal or external to the blood analyzing instrument. Waste circuit 128, and structures equivalent thereto, serve as means for disposing of excess fluid in the pipelining assembly.

After a blood sample is prepared in sample preparation chamber 121, the prepared blood sample is transferred to manifold 130 via fluid lines FL. (One of skill in the art would understand that transferring all of a prepared blood sample, or alternatively transferring a portion of the prepared blood sample, would be equivalent actions in the context of the presented invention. One of skill in the art would also understand that the transfer of prepared blood sample can be done via structures equivalent to fluid lines FL.) Manifold 130 includes a first control valve 131, which is in fluid communication between first sample preparation chamber 121A and a first queuing chamber 141. (As used herein, the word "between" is meant in the functional context and not necessarily in the context of the physical location of the control valve. Notwithstanding, although the word "between" should not imply a physical location, a component can still be physically located intermediate two respective components.) Manifold 130 also includes a second control valve 132, which is in fluid communication between second sample preparation chamber 121B and a second queuing chamber 142. Control valves 131, 132 open and close the flow of fluid between each sample preparation chamber 121A, 121B and the respective queuing chamber 141, 142. The timing of the opening and closing of control valves 131, 132 is control by system control processor C. The configuration presented allows for the pipelining functions further described below. As such, the functional arrangement of control valves 131, 132 serves as means for performing parallel pipelining functions. Additional means for performing parallel pipelining functions include structures equivalent to control valves 131, 132. In one embodiment, the control valves are solenoid valves.

Each queuing chamber 141, 142 includes one or more queuing chamber ports 145 that provide vent, vacuum or pressure to actively manipulate the flow of fluid into and out of the respective queuing chamber 141, 142. Queuing chamber ports 145 can be hydraulic (i.e., liquid) driven or pneumatic (i.e., air) driven. Queuing chamber ports 145 can also be used to deliver diluent to respective queuing chambers 141, 142 in order to clean the queuing chamber.

System control processor C controls the vent, vacuum, and/or pressure functions of queuing chamber ports 145. In one operational example, first control valve 131 can be set open and a vacuum can be applied through one or more of queuing chamber ports 145 in first queuing chamber 141. Such vacuum would draw prepared blood sample from first sample preparation chamber 121A into first queuing chamber 141. Similarly, if second control valve 132 is set open, a vacuum can be applied through one or more of queuing chamber ports 145 in second queuing chamber 142 to draw prepared blood sample from second sample preparation chamber 121B into second queuing chamber 142. As such, queuing chamber ports 145 and appropriate vent, vacuum, and/or pressure sources serve as means for directing the flow of a prepared blood sample from one of the sample preparation chambers to one of the queuing chambers. Additional means for directing the flow of a prepared blood sample from one of the sample preparation chambers to one of the queuing chambers include structures equivalent to queuing chamber ports 145 and appropriate vent, vacuum, and/or pressure sources. For example, in alternative embodiments, appropriately placed pressure sources may be employed to direct the flow of an aliquot of prepared blood sample from one of the sample preparation chambers to one of the queuing chambers. Further, in yet another alternative embodiment, queuing chamber ports 145 can be used to prime the flow of fluid into the respective queuing chamber in order to create a precise volume of prepared blood sample within respective queuing chamber. As used herein, to transfer or draw prepared blood sample from the sample preparation chamber to the queuing chamber should not be limited to a specific amount of prepared blood sample. In other words, all of, or only a portion of, the prepared blood sample in the sample preparation chamber can be transferred or drawn to the queuing chamber.

Use of queuing chambers 141, 142 in manifold 130 provides a place for temporary placement of a prepared blood sample prior to analysis. Meanwhile, the respective sample preparation chambers 121A, 121B can be cleaned and readied for a subsequent blood sample. For example, once a prepared blood sample is transferred from sample preparation chambers 121A, 121B, the respective control valve 131, 132 can be closed and the sample preparation chamber can be rinsed with water, diluent, and/or cleansing fluid. As such, the cleaning of the sample preparation chambers can be performed concurrently (i.e., in parallel) to the analysis of the prepared blood sample. Typically, prior instruments required the steps of processing, analysis and cleaning to be conducted in senes.

Queuing chambers 141, 142 are also coupled to waste circuit 128. Pressure from queuing chamber ports 145 can deliver excess fluid, such as excess sample fluid or cleansing fluid, to waste circuit 128. Vacuum from queuing chamber ports 145 can also be used to draw cleansing fluid into the queuing chamber. In alternative embodiments, pressure and vacuum sources, originating from waste circuit 128, can be used to deliver cleansing fluid to the queuing chamber, and thereafter withdraw the excess fluid from the queuing chamber.

Manifold 130 further includes a third control valve 133 and a fourth control valve 134. Control valves 133, 134 are in fluid communication between queuing chambers 141, 142 and a common fluid line CFL. As such, opening and closing of control valves 133, 134 permits the respective opening and shutting-off of fluid flow between queuing chamber 141, 142 and common fluid line CFL. In operation, for example, first control valve 131 and fourth control valve 134 can be set to a closed position, while third control valve 133 is set to an open position. Then, a pressure can be applied via queuing chamber ports 145 in first queuing chamber 141. The applied pressure will then transmit an aliquot of prepared blood sample within first queuing chamber through common fluid line CFL and into analysis chamber 150. Similarly, with second control valve 132 and third control valve 133 set to a closed position, and fourth control valve 134 set to an open position, pressure can be applied via queuing chamber ports 145 in second queuing chamber 142 to transmit an aliquot of prepared blood sample from second queuing chamber 142 to analysis chamber 150. In alternative embodiments, structures equivalent to the above described control valves 133, 134 and common fluid line CFL can be used to transfer aliquots of prepared blood sample from queuing chambers 141, 142 to analysis chamber 150. The term "aliquot" is used herein in accordance with common parlance. However, in the context of the presented invention, to transfer the entire prepared blood sample from the queuing chamber to the analysis chamber is equivalent to transferring an aliquot of prepared blood sample.

Analysis chamber 150 can be one of many exemplary analysis chambers. One example of an analysis chamber is a flow cell as depicted in the '652 patent, which is hereby incorporated by reference in its entirety, and more specifically for its disclosure of a multi-parameter transducer and analyzer. Analysis chamber 150 can include components for measuring DC impedance, RF conductivity, light scattering, and/or fluorescence characteristics of a prepared blood sample. (For simplicity, such measuring components are not shown.) As such, analysis chamber 150, and structures equivalent thereto, serve as means for analyzing the prepared blood sample. The output of analysis chamber 150 is coupled to waste circuit 128.

Extending from the analysis chamber 150 is a priming port 151. Flow of fluid through priming port 151 is controlled by pump 126 and system control processor C. Diluent fluid 152 can flow in or out of priming port 151 via pump 126. For example, in priming mode, prepared blood sample is drawn from one of the queuing chambers 141, 142, through the common fluid line CFL, and into the priming port 151. Once the common fluid line CFL is sufficiently primed, pressure from queuing chamber ports 145 drives an aliquot of prepared blood sample through analysis chamber 150. Fluidics within analysis chamber 150 provide sheath fluid for performing measurements within the interrogation zone of analysis chamber 150. (For simplicity, the fluidics are not shown.) After the analysis is completed, the flow of fluid through priming port 151 is reversed and diluent fluid 152 is delivered through priming port 151 to clean the common fluid line CFL. In an alternative embodiment, the priming port 151 can extend from the common fluid line CFL at manifold 130.

In operation, pipelining assembly 100 can be used to process a plurality of prepared blood samples through a blood analyzing instrument and perform parallel pipelining functions to increase the throughput of the blood analyzing instrument. For example, the chamber/valve configuration of pipelining assembly 100 allows for concurrently performed parallel processes. As used herein, when a step is said to be "performed concurrently" with another step, it is intended to mean that at least a portion of a first step overlaps in time with at least a portion of a second step. For example, if step (a) begins at time t=0 sec, and ends at time t=20 sec; and if step (b) begins at time t=15 sec, and ends at time t=25 sec; then steps (a) and (b) are understood to be "performed concurrently." Notwithstanding, the phrase "performed concurrently" can also be interpreted to mean that both steps begin and end at the same time.

For example, in one embodiment, the step of preparing a first prepared blood sample in first sample preparation chamber 121A is performed concurrently with the step of preparing a second prepared blood sample in second sample preparation chamber 121B. It is envisioned that once pipelining assembly 100 is under continuous operation, subsequent prepared blood samples from second sample preparation chamber 121B will lag behind prepared blood samples from first sample preparation chamber 121A. As such, in an embodiment, the step of transferring a second prepared blood sample from second sample preparation chamber 121B to second queuing chamber 142 is performed concurrently with the step of transferring a first prepared blood sample from first queuing chamber 141 to analysis chamber 150. Meanwhile, the step of cleaning first sample preparation chamber 121A can be performed concurrently with the step of transferring a first prepared blood sample from first queuing chamber 141 to analysis chamber 150. After cleaning first sample preparation chamber 121A, a third blood sample can be prepared in first sample preparation chamber 121A. The step of transferring the third prepared blood sample from first sample preparation chamber 121A to first queuing chamber 141 can be performed concurrently with the step of transferring the second prepare blood sample from second queuing chamber 142 to analysis chamber 150. Likewise, the steps of cleaning second sample preparation chamber 121B and preparing a fourth prepared blood sample in second sample preparation chamber 121B can be performed concurrently with the steps of transferring the second prepared blood sample from second queuing chamber 142 to analysis chamber 150 for analysis of the second prepared blood sample. One of skill in the art would understand that these parallel processes can be continued ad infinitum with the result of increased throughput of the blood analyzing instrument.

FIG. 2 is a schematic view of a pipelining assembly 200, in accordance with an alternative embodiment presented herein. Pipelining assembly 200 is similar to pipelining assembly 100 shown in FIG. 1. However, the schematic shown in FIG. 2 is provided to show the availability of using three or more sample preparation assemblies 220. Multiple sample preparation assemblies 220 allow for random access of prepared blood samples. As such, an operational program can be designed wherein prepared blood samples that have different preparation times can be accessed on a when-ready basis.

In the embodiment shown in FIG. 2, pipelining assembly 200 includes a first sample preparation chamber 221A, a second sample preparation chamber 221B, and a third sample preparation chamber 221C. In an alternative embodiment, a pipelining assembly can include a plurality of sample preparation chambers; i.e., 221A, 221B, 221C, ... 221*n*. Aspiration needle 116 is used to deliver whole blood sample to sample preparation chambers 221A, 221B, and 221C along track 119. After a blood sample is prepared in sample preparation chamber 221A, 221B, or 221C, prepared blood sample is transferred to one of queuing chambers 241, 242. In the embodiment shown, manifold 230 includes a first control valve 231, which is in fluid communication between first sample preparation chamber 221A and first queuing chamber 241. A second control valve 232 is in fluid communication between second sample preparation chamber 221B and second queuing chamber 242. A third control valve 233 is in fluid communication between third sample preparation chamber 221C and first queuing chamber 241. First control valve 231 and third control valve 233 are shown in a series arrangement. Alternative arrangements are available, as would be understood by one of skill in the art. The functional arrangement of control valves 231, 232, and 233, and structures equivalent thereto, serves as another example of means for performing parallel pipelining functions.

Manifold 230 also includes a fourth control valve 234, which is in fluid communication between first queuing chamber 241 and common fluid line CFL. Further, manifold 230 includes a fifth control valve 235, which is in fluid communication between second queuing chamber 242 and common fluid line CFL.

One of skill in the art would understand that while third sample preparation chamber 221C is shown in fluid communication with first queuing chamber 241, in an alternative embodiment, third sample preparation chamber 221C can be in fluid communication with second queuing chamber 242, or a third queuing chamber (not shown).

Figure 3:
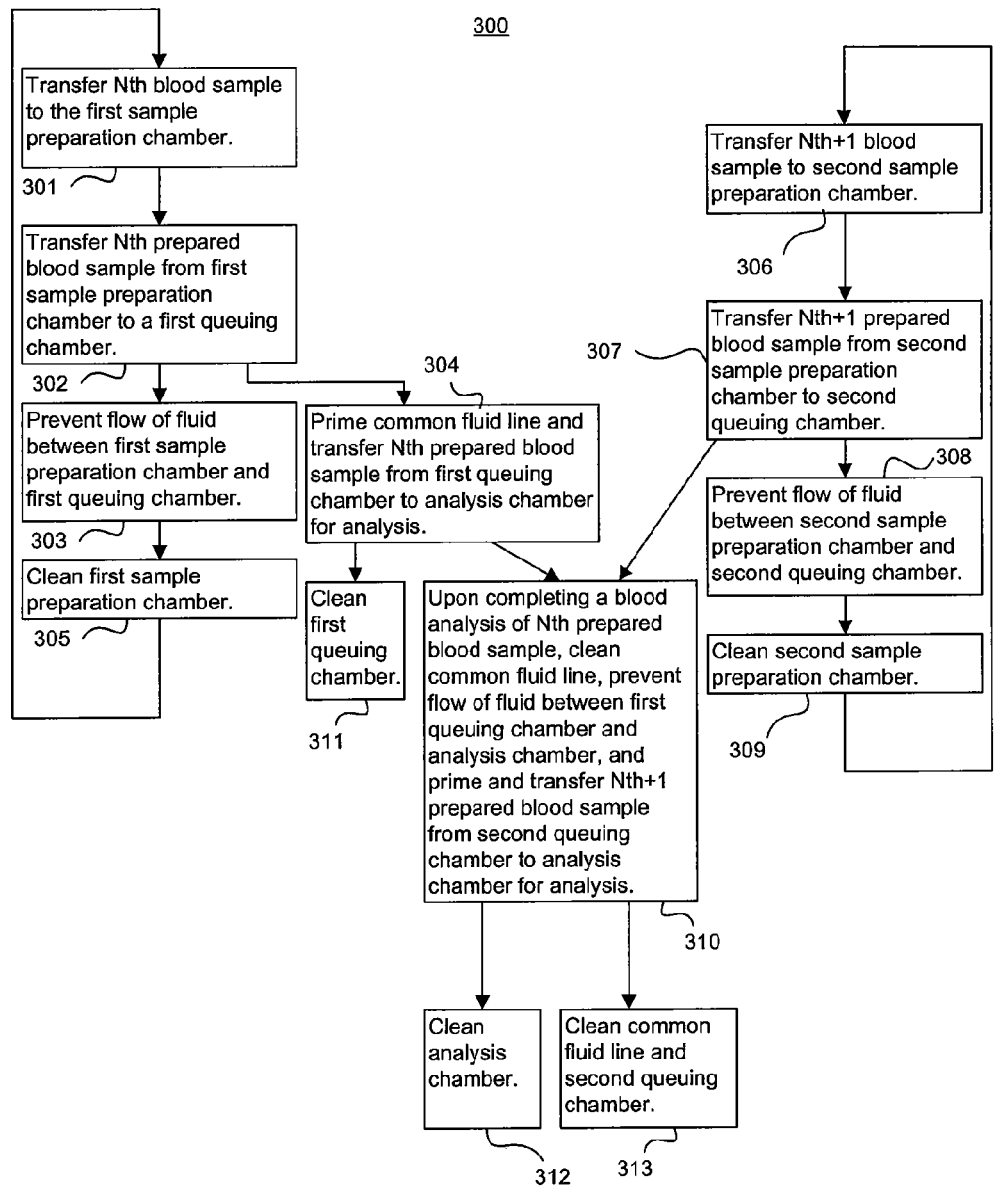
FIG. 3 is a flow chart illustrating one method presented herein.

FIG. 3 is a flow chart illustrating a method 300 in accordance with one embodiment presented herein. The flow chart of FIG. 3 further illustrates the parallel pipelining functions of pipelining assembly 100 of FIG. 1. To begin, in step 301, a first (or Nth) whole blood sample is transferred to first sample preparation chamber 121A for preparation. In step 302, the Nth prepared blood sample is transferred from first sample preparation chamber 121A to first queuing chamber 141. In step 303, the flow of fluid is prevented between first sample preparation chamber 121A and first queuing chamber 141. In step 305, first sample preparation chamber 121A is cleaned. The process flow for first sample preparation chamber 121A then returns to step 301 for a subsequent iteration.

In step 304, common fluid line CFL is primed and an aliquot of the Nth prepared blood is transferred from first queuing chamber 141 to analysis chamber 150. (As discussed above, in the context of this invention, to transfer all of the prepared blood sample is equivalent to transferring "an aliquot of" the prepared blood sample.) Step 304 can be performed concurrently with step 305. It is not important whether step 304 begins before or after step 305. In step 311, first queuing chamber 141 is cleaned. In one embodiment, first queuing chamber 141 is cleaned independent of common fluid line CFL. In another embodiment, first queuing chamber is cleaned after completion of the blood analysis. In such embodiment, the flow of fluid is reversed through common fluid line CFL and diluent fluid 152 is delivered from priming port 151 to the first queuing chamber 141. After diluent fluid 152 is delivered to first queuing chamber 141, third control valve 133 can be closed and the excess fluid in the first queuing chamber 141 can be discarded via waste circuit 128. In an alternative embodiment, first queuing chamber 141 is cleaned independent of the cleaning of common fluid line CFL.

In parallel to steps 301-305, a Nth+1 whole blood sample is transferred to second sample preparation chamber 121B for preparation, in step 306. In step 307, the Nth+1 prepared blood sample is transferred from second sample preparation chamber 121B to second queuing chamber 142. In step 308, the flow fluid is prevented between second sample preparation chamber 121B and second queuing chamber 142. Second sample preparation chamber 121B is then cleaned in step 309. After completion of step 309, the process flow for second sample preparation chamber 121B then returns to step 306 for a subsequent iteration.

In step 310, upon completing a blood analysis of an aliquot of the Nth prepared blood sample, the flow of fluid is reversed and diluent fluid 152 is delivered through priming port 151 and into common fluid line CFL. As discussed above, in one embodiment, diluent fluid 152 is delivered through common fluid line CFL and into first queuing chamber 141, thus cleaning common fluid line CFL and first queuing chamber 141 together (i.e., combining steps 310 and 311). In an alternative embodiment, common fluid line CFL can be cleaned independent of first queuing chamber 141. After cleaning common fluid line CFL, the flow of fluid is prevented between first queuing chamber 141 and analysis chamber 150, common fluid line CFL is primed, and an aliquot of the Nth+1 prepared blood sample is transferred from second queuing chamber 142 to analysis chamber 150. In step 313, common fluid line CFL and second queuing chamber 142 are cleaned. In one embodiment, step 313 includes cleaning common fluid line CFL and second queuing chamber 142 by reversing the flow of fluid through common fluid line CFL and delivering diluent fluid 152 through priming port 151 and into second queuing chamber 142. In an alternative embodiment, second queuing chamber 142 and common fluid line CFL are cleaned independent of one another. Optionally, in step 312, analysis chamber 150 is cleaned. In one embodiment, the cleaning of analysis chamber 150 can be skipped because common fluid line CFL cleaning and priming sufficiently prevents cross-contamination between subsequent prepared samples. Further, in one embodiment, the continuous flow of sheath fluid through analysis chamber 150 functions to keep the analysis chamber clean.

The method 300 of FIG. 3 continues to subsequent iteration as a continuous loop until all blood sample are processed. Any one of steps 301-305 and 311 can be performed concurrently with any one of steps 306-309. Any one of steps 301-303, 305 and 311 can be performed concurrently with step 310-313. Any one of steps 306-309 can be performed concurrently with step 304. These steps can be performed in an ad infinitum loop, wherein the parallel pipelining of fluid ultimately increases the throughput of the blood analyzing instrument.

EXAMPLES

The following paragraphs serve as examples of the above-described embodiments.

Example 1

In one embodiment, there is provided a pipelining assembly for a blood analyzing instrument comprising a first sample preparation chamber, a first queuing chamber in fluid communication with the first sample preparation chamber, and a first control valve between the first sample preparation chamber and the first queuing chamber and adapted to control the flow of fluid between the first sample preparation chamber and the first queuing chamber. The pipelining assembly further comprises a second sample preparation chamber, a second queuing chamber in fluid communication with the second sample preparation chamber, a second control valve between the second sample preparation chamber and the second queuing chamber and adapted to control the flow of fluid between the second sample preparation chamber and the second queuing chamber, and an analysis chamber in fluid communication with the first queuing chamber and the second queuing chamber. In one embodiment, the first and second control valves are solenoid valves. In one embodiment, the pipelining assembly further comprises a third control valve between the first queuing chamber and the analysis chamber and adapted to control the flow of fluid between the first queuing chamber and the analysis chamber. In yet another embodiment, the pipelining assembly further comprises a fourth control valve between the second queuing chamber and the analysis chamber and adapted to control the flow of fluid between the second queuing chamber and the analysis chamber. In one embodiment, the pipelining assembly further includes a hydraulic system in fluid communication with the pipelining assembly to manipulate the movement of fluid through the pipelining assembly.

In an alternative embodiment, the pipelining assembly includes a third sample preparation chamber in fluid communication with one of the queuing chambers. The pipelining assembly can further include a third queuing chamber in fluid communication with the analysis chamber. Further, the pipelining assembly can include a priming outlet extending from a common fluid line, wherein the common fluid line links the first and second queuing chambers to the analysis chamber. In one embodiment, the priming outlet extends from the analysis chamber. In another embodiment, the priming outlet extends from the manifold. In alternative embodiment, the pipelining assembly includes a waste circuit or other means for disposing of excess fluid in the pipelining assembly.

Example 2

In one embodiment, there is provided a blood analyzing instrument comprising means for receiving a blood sample, means for separating the blood sample into a plurality of sample preparation chambers, and at least two queuing chambers. The blood analyzing instrument further comprises means for directing the flow of a prepared blood sample from one of the sample preparation chambers to one of the queuing chambers, means for analyzing the prepared blood sample, and means for performing parallel pipelining functions.

Example 3

In one embodiment, there is provided a method of processing a plurality of prepared blood samples through a blood analyzing instrument. The method includes the following steps: (a) transferring an aliquot of a first prepared blood sample from a first sample preparation chamber to a first queuing chamber; (b) preventing the flow of fluid between the first sample preparation chamber and the first queuing chamber; (c) transferring the first prepared blood sample from the first queuing chamber to an analysis chamber for analysis; (d) cleaning the first sample preparation chamber; (e) transferring an aliquot of a second prepared blood sample from a second sample preparation chamber to a second queuing chamber; (f) preventing the flow of fluid between the second sample preparation chamber and the second queuing chamber; (g) cleaning the second sample preparation chamber; (h) upon completion of step (c), cleaning a path between the analysis chamber and the first queuing chamber; (i) cleaning the first queuing chamber; (j) preventing the flow of fluid between the first queuing chamber and the analysis chamber and transferring the second prepared blood sample from the second queuing chamber to the analysis chamber for analysis; (k) transferring an aliquot of a third prepared blood sample to the first queuing chamber; (l) upon completion of step 0), cleaning a path between the analysis chamber and the second queuing chamber; (m) cleaning the second queuing chamber; and (n) preventing the flow of fluid between the second queuing chamber and the analysis chamber and transferring the third prepared blood sample from the first queuing chamber to the analysis chamber; wherein step (e) is performed concurrently with step (c); wherein step (k) is performed concurrently with step (j).

In alternative embodiments, step (d) is performed concurrently with step (c), step (f) is performed concurrently with step (c), step (g) is performed concurrently with step (c), step (g) is performed concurrently with step (d), and/or step (g) is performed concurrently with step (j). Further, in alternative embodiments, step (i) is performed concurrently with step (h), and/or step (m) is performed concurrently with step (l). Further still, in alternative embodiments, step (c) includes priming the path between the first queuing chamber and the analysis chamber, step (j) includes priming the path between the second queuing chamber and the analysis chamber and/or step (n) includes priming the path between the first queuing chamber and the analysis chamber.

Example 4

In one embodiment, there is provided a pipelining assembly for a blood analyzing instrument comprising at least two queuing chambers, wherein each queuing chamber has an input and an output, a plurality of sample preparation chambers, wherein the input of each queuing chamber is connected to at least one of the sample preparation chambers, and an analysis chamber connected to an output of each queuing chamber. The pipelining assembly further comprises means for performing parallel pipelining functions. In one embodiment, the parallel pipelining functions include transfer of a first prepared blood sample from one queuing chamber to the analysis chamber for processing through the analysis chamber while a second prepared blood sample is transferred to a second queuing chamber. In another embodiment, the parallel pipelining functions include transfer of a prepared blood sample from one queuing chamber to the analysis chamber for processing through the analysis chamber while a second queuing chamber is cleaned. In yet another embodiment, the parallel pipelining functions include transfer of a prepared blood sample from one queuing chamber to the analysis chamber for processing through the analysis chamber while at least one sample preparation chamber is cleaned. In one embodiment, the means for performing parallel pipelining functions includes a plurality of control valves. In one embodiment, the means for performing parallel pipelining functions includes a hydraulic circuit for controlling fluid flow through the pipelining assembly.

Examples 5-7

In examples 5-7, pipelining assembly 100 of FIG. 1 can be used to support the ability to run one or more hematology tests, such as a Differential test (D), a NRBC test (N) and a Reticulocyte test (R). Samples for each test are prepared in external sample preparation chambers and transferred to first and second queuing chambers to be processed through a flow cell in a sequential manner.

Example 5

In one example, pipelining assembly 100 is provided to perform a Differential test on three whole blood samples. The method for performing such Differential test includes the following steps: (a) transferring Differential Prepared Sample 1 (D-PS1) into a first queuing chamber; (b) processing D-PS1 through the flow cell; (c) in parallel to step (b), transferring Differential Prepared Sample 2 (D-PS2) into a second queuing chamber; (d) upon completion of analysis of D-PS1, processing D-PS2 through the flow cell; (e) in parallel to step (d), cleaning the first queuing chamber, followed by transfer of Differential Prepared Sample 3 (D-PS3) into the first queuing chamber; (f) upon completion of analysis of D-PS2, processing D-PS3 through the flow cell; (g) in parallel to step (f), cleaning the second queuing chamber; and (h) upon completion of analysis of D-PS3, cleaning the first queuing chamber to complete the cycle.

Example 6

In another example, pipelining assembly 100 is provided to perform NRBC/Differential tests on two whole blood samples. The method for performing NRBC/Differential tests on two whole blood specimen includes the following steps: (a) transferring NRBC Prepared Sample 1 (N-PS1) into a first queuing chamber; (b) processing N-PS1 through the flow cell; (c) in parallel to step (b), transferring Differential Prepared Sample 1 (D-PS1) into the second queuing chamber; (d) upon completion of analysis of N-PS1, processing D-PS1 through the flow cell; (e) in parallel to step (d), cleaning the first queuing chamber, followed by transferring of NRBC Prepared Sample 2 (N-PS2) into the first queuing chamber; (f) upon completion of analysis of D-PS1, processing N-PS2 through the flow cell; (g) in parallel to step (f), cleaning the second queuing chamber, followed by transferring of Differential Prepared Sample 2 (D-PS2) into the second queuing chamber; (h) upon completion of analysis of N-PS2, processing D-PS2 through the flow cell; (i) in parallel to step (h), cleaning the first queuing chamber; and (j) upon completion of analysis of D-PS2, cleaning the second queuing chamber to complete the cycle.

Example 7

In another example, pipelining assembly 100 is provided to perform NRBC/Differential/Reticulocytes tests on two whole blood samples. The method for performing NRBC/Differential/Reticulocytes tests on two whole blood specimens includes the following steps: (a) transferring NRBC Prepared Sample 1 N-PS1 into the first queuing chamber; (b) processing N-PS1 through the flow cell; (c) in parallel to step (b), transferring Differential Prepared Sample 1 (D-PS1) into the second queuing chamber; (d) upon completion of analysis of N-PS1, processing D-PS1 through the flow cell; (e) in parallel to step (d), cleaning the first queuing chamber, followed by transferring of Reticulocytes Prepared Sample 1 (R-PS1) into the first queuing chamber; (f) upon completion of analysis of D-PS1, processing R-PS1 through the flow cell; (g) in parallel to step (f), cleaning the second queuing chamber, followed by transfer of NRBC Prepared Sample 2 (N-PS2) into the second queuing chamber; (h) upon completion of analysis of R-PS1, processing N-PS2 through the flow cell; (i) in parallel to step (h), cleaning the first queuing chamber, followed by transfer of Differential Prepared Sample 2 (D-PS2) into the first queuing chamber; (j) upon completion of analysis of N-PS2, processing D-PS2 through the flow cell; (k) in parallel to step (j), cleaning the second queuing chamber B, followed by transferring of Reticulocytes Prepared Sample 2 (R-PS2) into the second queuing chamber; (l) upon completion of analysis of D-PS2, processing R-PS2 through the flow cell; (m) in parallel to step (l) cleaning the first queuing chamber; and (n) upon completion of analysis of R-PS2, cleaning the second queuing chamber to complete cycle.

In example 8, pipelining assembly 200 of FIG. 2 can be used to support the ability to run one or more hematology tests, such as a Differential test (D), a NRBC test (N) and a Reticulocyte test (R). Example 8 takes advantage of the random access capabilities of pipelining assembly 200. Random access capabilities reduce flow cell idle time by processing next-available prepared blood samples through the flow cell regardless of sample preparation order. Samples for each test are prepared in external sample preparation chambers and transferred to first and second queuing chambers to be processed through a flow cell in a sequential manner.

Example 8

In one example, pipelining assembly 200 is provided to perform NRBC/Differential tests on two whole blood samples and a CD4 test on the first whole blood sample. The CD4 test generally has a longer preparation and incubation time relative to the NRBC/Differential test preparations and therefore, in this example, gets prepared first.

The method for performing such NRBC/Differential/CD4 tests includes the following steps: (a) preparing and incubating a CD4 Prepared Sample 1 (CD4-PS1) in a sample preparation chamber; (b) transferring NRBC Prepared Sample 1 (N-PS1) into the first queuing chamber; (c) process N-PS1 through the flow cell; (d) in parallel to step (c), transferring Differential Prepared Sample 1 (D-PS1) into the second queuing chamber; (e) upon completion of N-PS1, processing D-PS1 through the flow cell; (f) in parallel to step (e) cleaning the first queuing chamber, followed by transferring of NRBC Prepared Sample 2 (N-PS2) into the first queuing chamber; (g) upon completion of D-PS1, processing N-PS2 through the flow cell; (h) in parallel to step (g), cleaning the second queuing chamber, followed by transfer of CD4 Prepared Sample 1 (CD4-PS1) into the second queuing chamber; (i) upon completion of N-PS2, processing CD4-PS1 through the flow cell; (j) in parallel to step (i), cleaning the first queuing chamber A, followed by transferring of Differential Prepared Sample 2 (D-PS2) into the first queuing chamber; (k) upon completion of CD4-PS1, processing D-PS2 through the flow cell; (l) in parallel to step (k), cleaning the second queuing chamber; and (m) upon completion of D-PS2, cleaning the first queuing chamber to complete cycle.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

The invention claimed is:

1. A method of processing a plurality of samples through an instrument, the method comprising:
   (a) transferring a first sample from a first chamber to a second chamber through a first control valve;
   (b) closing off the first control valve, opening a second control valve, and applying a pressure to a first port of the second chamber to transfer an aliquot of the first sample from the second chamber through the second control valve to an analysis chamber for analysis;
   (c) opening a third control valve to transfer a second sample from a third chamber to a fourth chamber through the third control valve, wherein step (c) is performed substantially concurrently with step (b);
   (d) transferring an aliquot of the second sample from the fourth chamber to the analysis chamber for analysis; and
   (e) cleaning the first chamber substantially concurrently with step (b).

2. The method of claim 1, further comprising (f) delivering a fluid to the first port to clean the first chamber.

3. The method of claim 1, wherein step (e) is performed substantially concurrently with step (d).

4. The method of claim 1, wherein step (e) is performed concurrently with step (c).

5. The method of claim 1, wherein step (e) is performed substantially concurrently with step (b).

6. The method of claim 1, further comprising:
   (f) transferring a third sample from the first chamber to the second chamber, wherein step (f) is performed concurrently with step (d).

7. The method of claim 6, further comprising:
   (g) cleaning the third chamber, wherein step (g) is performed substantially concurrently with step (d).

8. The method of claim 7, further comprising:
   (h) transferring a fourth blood sample to the third chamber, wherein step (h) is performed substantially concurrently with step (d).

9. A method of processing a plurality of samples through a particle analyzing instrument, comprising:
   (a) transferring a first sample from a first sample preparation chamber to a first queuing chamber through a first control valve;
   (b) transferring an aliquot of the first sample from the first queuing chamber to an analysis chamber for analysis by applying a first pressure to the first queuing chamber through a first port and closing off the first control valve, wherein the first port and the first control valve are in connection with the first queuing chamber;
   (c) transferring a second sample from a second sample preparation chamber to a second queuing chamber by applying a second pressure to the second queuing chamber through a second port and opening a second control valve, wherein the second port and the second control valve are in connection with the second queuing chamber;
   (d) transferring an aliquot of the second sample from the second queuing chamber to the analysis chamber for analysis, wherein step (c) is performed substantially concurrently with step (b); and
   (e) cleaning the first sample preparation chamber, wherein step (e) is performed concurrently with step (b).

10. The method of claim 9, wherein the first pressure is a positive pressure.

11. The method of claim 9, wherein the second pressure is a negative pressure.

12. The method of claim 9, wherein the first port and second port are located at the top of the first queuing chamber and the second queuing chamber, respectively.

13. The method of claim 9, further comprising:
   (f) cleaning the second sample preparation chamber;
   (g) upon completion of step (b), cleaning a path between the analysis chamber and the first queuing chamber;
   (h) cleaning the first queuing chamber;
   (i) upon completion of step (d), cleaning a path between the analysis chamber and the second queuing chamber; and
   (j) cleaning the second queuing chamber.

14. The method of claim 13, wherein step (d) is performed substantially concurrently with step (f).

15. The method of claim 13, wherein step (d) is performed substantially concurrently with step (h).

16. The method of claim 13, further comprising: (k) transferring an aliquot of a third sample to the first queuing chamber.

17. The method of claim 16, wherein step (k) is performed substantially concurrently with step (d).

18. The method of claim 13, further comprising: priming the path between the first queuing chamber and the analysis chamber prior to step (b).

19. The method of claim 13, further comprising: priming the path between the second queuing chamber and the analysis chamber prior to step (d).

20. The method of claim 9, wherein the samples are biological samples containing particles and cells.

* * * * *